United States Patent [19]  
Adelstein

[11] 4,239,908  
[45] Dec. 16, 1980

[54] N-ARALKENYL-N'-CYANO-N''-(HETEROCYCLYLTHIOALKYL)-GUANIDINES

[75] Inventor: Gilbert W. Adelstein, Evanston, Ill.

[73] Assignee: G.D. Searle & Co., Skokie, Ill.

[21] Appl. No.: 101,923

[22] Filed: Dec. 10, 1979

[51] Int. Cl.³ ............... C07D 263/34; C07D 233/54; C07D 277/26; C07D 307/38

[52] U.S. Cl. .................. 542/416; 424/270; 424/272; 424/273 R; 424/285

[58] Field of Search ........................ 542/416

[56] References Cited

U.S. PATENT DOCUMENTS

| 3,950,333 | 4/1976 | Durant et al. | 424/251 X |
| 3,950,353 | 4/1976 | Durant et al. | 424/263 X |
| 4,018,931 | 4/1977 | Durant et al. | 424/263 X |
| 4,049,669 | 9/1977 | Lam et al. | 548/119 |
| 4,056,621 | 11/1977 | Brown et al. | 548/336 |
| 4,128,658 | 12/1978 | Price et al. | 260/347.2 |
| 4,154,844 | 5/1979 | Durant et al. | 548/138 X |

FOREIGN PATENT DOCUMENTS

| 867594 | 2/1978 | Belgium | 260/347.2 |
| 857388 | 11/1978 | Belgium | 548/342 |

OTHER PUBLICATIONS

Chemical Abstracts, vol. 80, abst. 46,168j (1974) (abst. of Durant et al., Ger. Offen. 2,349,779).

*Primary Examiner*—John D. Randolph  
*Attorney, Agent, or Firm*—Albert Tockman

[57] ABSTRACT

N-aralkenyl-N'-cyano-N''-(heterocyclylthioalkyl)-guanidines and salts thereof which are pharmacologically active as inhibitors of gastric secretion and their preparation from isothioureas are disclosed.

16 Claims, No Drawings

N-ARALKENYL-N'-CYANO-N''-(HETEROCYCLYL-THIOALKYL)-GUANIDINES

The present invention is a pharmacologically active N-aralkenyl-N'-cyano-N''-(heterocyclylthioalkyl)-guanidine of formula I and pharmacologically acceptable salts thereof.

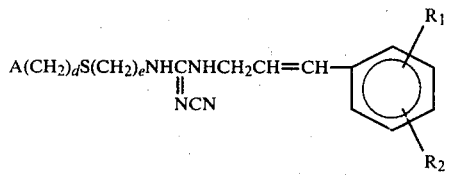

In formula I, A is an imidazolyl, oxazolyl, thiazolyl or furyl radical of the formulas II, III or IV.

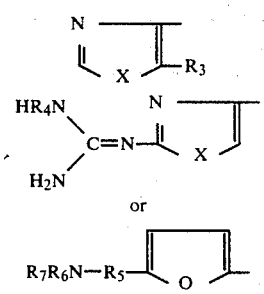

$R_1$ and $R_2$ may be the same or different and each represents hydrogen, halogen, hydroxy, trifluoromethyl or straight-chain or branched-chain alkoxy containing 1 to 7 carbon atoms and either unsubstituted or substituted by aryl or cycloalkyl. In addition, $R_1$ and/or $R_2$ can represent an amino radical either unsubstituted or substituted with at least one acyl radical or straight-chain or branched-chain alkyl radical, each containing 1 to 7 carbon atoms, and the alkyl radical being either unsubstituted or substistuted by aryl or cycloalkyl. In the alternative, $R_1$ and $R_2$ can be interconnected forming a group having terminal oxygen atoms which are separated by a methylene or ethylene radical and which are attached to adjacent carbon atoms on the phenyl ring in formula I.

In formulas II and III, X represents —O—, —S—, or —NH—. In addition, in formula II, $R_3$ represents hydrogen, halogen or straight-chain or branched-chain alkyl containing 1 to 7 carbon atoms. When X in formula III represents S or NH, $R_4$ represents hydrogen or straight-chain or branched-chain alkyl containing 1 to 7 carbon atoms. When X in formula III represents O, $R_4$ is hydrogen.

In formula IV, $R_5$ is a straight or branched alkylene chain of 1 to 6 carbon atoms, and $R_6$ and $R_7$ can be the same or different and each represents hydrogen, cycloalkyl or straight or branched-chain alkyl unsubstituted or substituted by aryl, each containing 1 to 7 carbon atoms. In the alternative, $R_6$ and $R_7$ can be interconnected and can contain oxygen, as tetramethylene, pentamethylene, methyleneoxyethylene, methyleneoxytrimethylene or ethyleneoxyethylene, to form together with the nitrogen atom in formula III a 5- or 6-membered heterocyclic ring.

In formula I, when A is of formula II or IV, d is 0, 1 or 2 and e is 2 or 3. When A is of formula III and X represents S or NH, d is 1 or 2 and e is 2 or 3. When A is of formula III and X is O, d is 1 and e is 2. In all cases, the sum of d and e is 3 or 4.

Halogen radicals suitable as $R_1$, $R_2$ and $R_3$ include fluorine, chlorine, bromine and iodine. Alkoxy radicals suitable as $R_1$ and $R_2$ include methoxy, ethoxy, cyclohexylmethoxy, phenylmethoxy and n-propoxy, n-butoxy, n-hexoxy and n-heptoxy and their branched-chain isomers. Alkyl radicals suitable as $R_3$, $R_4$, $R_6$ and $R_7$ and as substituents in the amino radicals of $R_1$ and $R_2$ include methyl, ethyl, n-propyl, n-butyl, n-pentyl, n-hexyl and n-heptyl and their branched-chain isomers, as well as phenylmethyl and cyclohexylmethyl. Additional alkyls suitable as substituents on the amino of $R_1$ and $R_2$ are phenylmethyl, cyclohexylmethyl, cyclopentylmethyl and cyclopentylethyl. Additional alkyls suitable as $R_6$ and $R_7$ include cyclopentyl, cyclohexyl and phenylmethyl. Acyl radicals suitable as substituents in the amino radicals of $R_1$ and $R_2$ include acetyl, propionyl, butyryl, valeryl, caproyl, enanthyl, and benzoyl.

Preferably in formula I, d is 1, and/or e is 2, and/or the sum of d and e is 3. It is also preferred that $R_1$ and/or $R_2$ is hydrogen, hydroxy, halogen, methoxy, phenylmethoxy or amino substituted with acetyl, methyl or phenylmethyl, and more preferably is mono-substituted, or alternatively that $R_1$ and $R_2$ are interconnected with the oxygen atoms therein separated by a methylene radical.

Preferably in formulas II and IV, X is NH and A is imidazolyl. It is also preferred that $R_3$ in formula II is hydrogen or methyl and that $R_4$ in formula III is hydrogen or methyl. $R_5$ in formula IV is preferably methylene. Also in preferred embodiments, $R_6$ and/or $R_7$ in formula IV is hydrogen or methyl—more preferably one of $R_6$ and $R_7$ is methyl and the other is hydrogen and most preferably both are methyl—or alternatively $R_6$ and $R_7$ are interconnected as tetramethylene or pentamethylene.

The novel compounds of the present invention are useful by reason of their valuable pharmacological properties as is exemplified by their ability to inhibit the gastric secretion stimulated by secretogogues such as histamine and pentagastrin while furthermore possessing the surprising advantges of lacking the potent undesirable side effects displayed by related substances.

One specific assay used to detect gastric antisecretory activity is described as follows. Adult female beagle dogs weighing 13-25 kilograms are prepared with denervated fundic Heidenhain pouches. After a recovery period of at least 4 weeks following surgery, the animals are fasted for approximately 20 hours, then are placed in Pavlov stands and infused intravenously with saline solution. The pouched secretions are collected every 15 minutes and measured for volume and total acidity by titration with 0.1 N sodium hydroxide to pH 7.0. Following a 30 minute basal secretion the dogs are infused with a saline solution of histamine dihydrochloride at a dose of 1.0 mg./hr. The volume of the diffusion is kept at approximately 13 ml./hr. A steady state plateau of gastric secretion is obtained approximately 1 hour following the start of histamine infusion at the end of which time the test compound dissolved in a solution of 30 percent by volume of propylene glycol and 20 percent by volume of ethanol in water is administered by a single intravenous injection bolus. The duration of the anti-secretory effects is determined and the side effects, if any, recorded. The compound is rated active if significant inhibition of secretory parameters occur following compound treatment.

A second specific assay used to detect gastric antisecretory activity is described as follows. Adult female beagle dogs weighing 7–10 kilorgams are prepared with Thomas-type gastric fistuls. After a recovery period of at least 4 weeks following surgery, the animals are fasted for approximately 20 hours, then are placed in Pavlov stands and infused intravenously with saline solution. The gastric secretions are collected every 15 minutes and measured for volume and total acidity by titration with 0.1 N sodium hydroxide to pH 7.0 Following a 30 minute basal secretion the dogs are infused with a saline solution of histamine dihydrochloride at a dose of 1.0 mg./hr. The volume of the diffusion is kept at approximately 6.5 ml./hr. A steady state plateau of gastric secretion is obtained approximately 1 hour following the start of histamine infusion, at the end of which time the test compound dissolved in a solution of 30 percent by volume of propylene glycol and 20 percent by volume of ethanol in water is administered intragastrically through a gastric dosage plug. The gastric cannula is then closed to allow sufficient contact time between the test compound and the gastric mucosa. After 30 minutes of contact time passes, the gastric cannula is opened and internal gastric secretion collections are taken. The duration of the anti-secretory effects is determined and the side effects, if any, recorded. The compound is rated active if statistically significant inhibition of secretory parameters occur following compound treatment.

A preferred compound of this invention, N-cyano-N'-[2-(((5-methyl-1H-imidazol-4-yl)methyl)thio)ethyl]-N"-(3-phenyl-2-propen-1-yl)guanidine was found to inhibit gastric secretions in both foregoing tests. Suitable dosages are in the range of 0.5 to 10 mg./kg/day when administered as hereinafore described.

The distinguishing response in dogs set forth above is of course intended merely to illustrate this aspect of the instant invention, and accordingly is not to be construed as either delimiting or exclusionary. Appropriate dosages in any given instance, of course, depend upon the nature and severity of the condition treated, the route of administration, and the species of mammal involved, including its size and any individual idiosyncrasies which obtain.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl ethers, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved or suspended in water or a comparably innocuous liquid. Parenteral administration may be effected via sterile fluid admixture with water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; see, for example, F. W. Martin et al., "Remington's Pharmaceutical Sciences", 14 Ed., Mack Publishing Company, Eaton, Pa., 1965.

Compounds of formula I when d is 1 or 2 can be prepared by a process involving reacting a heterocyclylalkylthioalkylamine of formula V and dimethyl N-cyano-dithioimidocarbonate, preferably in equimolar amounts, at room temperature in a protic or aprotic polar solvent such as an alcohol, acetonitrile, dimethylformamide or a water-alcohol mixture, to form an isothiourea of formula VI.

The isothiourea of formula VI is solidified by removal of the solvent or by precipitation induced by the addition of water to the solvent. The isothiourea then is reacted with an arylallylamine of formula VII, preferably in equimolar amounts, at elevated temperatures in the range of about 80° C. to about 130° C., to form a product of formula I. A protic or aprotic polar solvent is also used in this step.

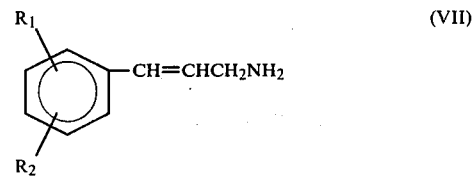

Alternatively the arylallylamine of formula VII is reacted with dimethyl N-cyanoimidodithiocarbonate at room temperature in a protic or aprotic polar solvent such as an alcohol, acetonitrile, dimethylformamide or a water-alcohol mixture, to form an isothiourea of formula VIII, which, after separation in solid form as described above, is then reacted with a heterocyclylalkylthioalkylamine, of formula V at elevated temperatures in the range of about 80° C. to about 130° C. to form a product of formula I.

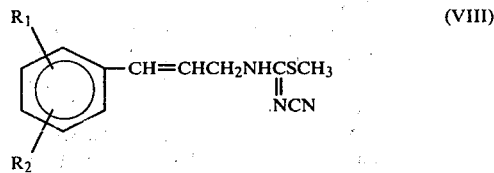

The protic or aprotic polar solvents noted above can be used in both steps of this alternative procedure.

In formulas V–VIII, A, d, e, $R_1$ and $R_2$ are defined in formulas I–IV.

Compounds of formula I when d is O can be prepared by a process involving reacting a heterocyclylthiol of formula IX with an N-(ω-bromoalkylphthalimide of formula X in alkaline methanol to form the alkylate of formula XI which is then reacted in ethanol with hydrazine to form a product of formula XII.

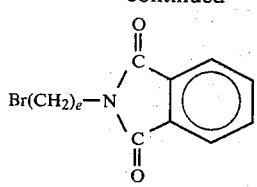

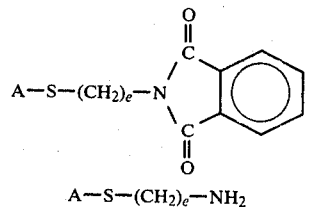

A—S—(CH$_2$)$_e$—NH$_2$ (XII)

In formulas IX–XII, A and e are as defined in formula I. The heterocyclylthioalkylamine of formula XII is then reached with a material of formula VIII to form a product of formula I wherein d is O.

Numerous examples of the starting material of formula VII are commercially available. Furthermore compounds of formula VII can be readily prepared by a process involving reacting an aldehyde of formula XIII, wherein R$_1$ and R$_2$ are as defined in formula I, with acetaldehyde in the presence of a base to form an unsaturated aldehyde of formula XIV, as reported in Faust and Sahyun, U.S. Pat. No. 3,094,561

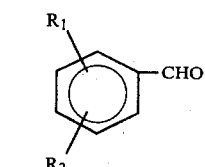

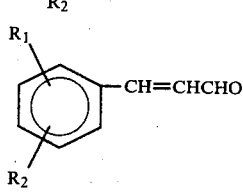

This unsaturated aldehyde is then selectively reduced, for example, with aluminum hydride in tetrahydrofuran, to form an unsaturated alcohol of formula XV, as reported in Jorgenson, Tet. Lett. 559(1962).

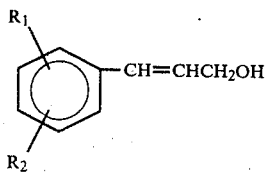

The alcohol is then converted to the corresponding chloride of formula XVI by reaction with concentrated hydrochloric acid or with thionyl chloride in toluene.

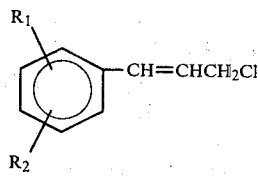

The chloride is then reacted with potassium phthalimide in ethanol to form the alkylate of formula XVII, which is reacted with hydrazine to form a product of formula VII, as reported in Gensler and Rockett, J.A.C.S. 77, p. 3262(1955).

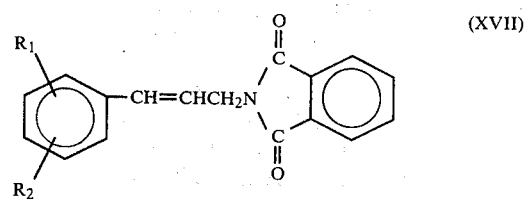

The present invention will be more clearly understood from the following specific examples. The following examples describe in detail compounds illustrative of the present invention and methods which have been used for their preparation.

EXAMPLE 1

To a 0.2 molar solution of 3-phenyl-2-propen-1-amine hydrochloride in ethanol was added potassium hydroxide in an amount equimolar with the hydrochloride, and the solution was stirred for 0.5 hour, forming the free amine and potassium chloride which crystallized and was removed by filtration. To the filtrate was added dimethyl-N-cyanoimidodithiocarbonate in an amount equimolar with the hydrochloride originally present in solution, and the resulting solution was stirred at room temperature overnight, forming N-cyano-N'-(3-phenyl-2-propen-1-yl)carbamimidothioic acid, methyl ester of formula XVIII. A volume of water equal to the volume of ethanol was then added to the solution and the methyl ester solidified and was filtered and dried. The dry product had a melting point of about 174°–176° C.

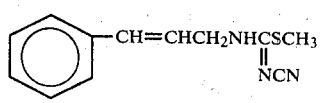

EXAMPLE 2

To a 0.2 molar solution of 2-[((5-methyl-1H-imidazol-4-yl)methyl)thio]ethanamine dihydrochloride of formula XIX

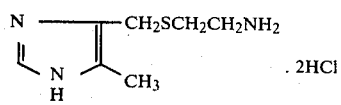

in a solvent containing 95 percent by volume of ethanol and 5 percent of water was added potassium hydroxide in twice the molar amount of the dihydrochloride, and the solution was stirred for 0.5 hour at room temperature, forming the free amine and potassium chloride which crystallized and was removed by filtration. To the filtrate was added the product of Example 1 in an amount equimolar with the dihydrochloride originally present in solution, and the resulting mixture was refluxed for 2.5 days, forming a mixture containing N-cyano-N'-[2-(((5-methyl-1H-imidazol-4-yl)methyl)-thio)ethyl]-N''-(3-phenyl-2-propen-1-yl)guanidine of formula XX as a product. Evaporation of the solvent resulted in a semisolid mixture which was then separated chromatographically on a silica gel column using an elution solvent of 8 percent by volume of methanol in methylene chloride. After unreacted isothiourea eluted, eluted fractions containing the aforesaid product were collected. Evaporation of the solvent therefrom afforded an oil which was then dissolved in acetonitrile and the solution was acidified with hydrochloric acid in isopropanol, forming an oil. After standing several days, hydrochloride crystals of the aforesaid guanidine formed, and the supernatant liquid was decanted. After stirring the crystals in boiling acetonitrile, this mixture was cooled and the crystals were filtered and dried. The product melted at about 129°–145° C.

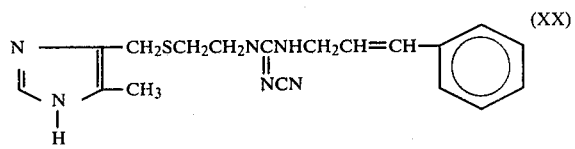

EXAMPLE 3

Repeating the procedure of Example 1 using 3-(4-hydroxyphenyl)-2-propen-1-amine hydrochloride instead of the hydrochloride therein, N-cyano-N'-[3-(4-hydroxyphenyl)-2-propen-1-yl]carbamimidothioic acid, methyl ester is formed as the product.

EXAMPLE 4

Repeating the procedure of Example 2 using 2-[((1H-imidazol-4-yl)methyl)thio]ethanamine dihydrochloride instead of the dihydrochloride therein and the product of Example 3 instead of the product of Example 1, N-cyano-N'-[3-(4-hydroxyphenyl)-2-propen-1-yl]-N''-[2-(((1H-imidazol-4-yl)-methyl)thio)ethyl]-guanidine hydrochloride is formed as the final product.

EXAMPLE 5

Repeating the procedure of Example 1 using 3-(4-chlorophenyl)-2-propen-1-amine hydrochloride instead of the hydrochloride therein, N-[3-(4-chlorophenyl)-2-propen-1-yl]-N'-cyanocarbamimidothioic acid, methyl ester is formed as the product.

EXAMPLE 6

Repeating the procedure of Example 2 using 3-[((5-chloro-1H-imidazol-4-yl)methyl)thio]-propan-1-amine dihydrochloride instead of the dihydrochloride therein and the product of Example 5 instead of the product of Example 1, N-[3-(((5-chloro-1H-imidazol-4-yl)methyl)-thio)prop-1-yl]-N'-[3-(4-chlorophenyl)-2-propen-1-yl]-N''-cyanoguanidine hydrochloride as the final product.

EXAMPLE 7

Repeating the procedure of Example 1 using 3-(4-methoxyphenyl)-2-propen-1-amine hydrochloride instead of the hydrochloride therein, N-cyano-N'-[3-(4-methoxyphenyl)-2-propen-1-yl]carbamimidothioic acid, methyl ester is formed as the product.

EXAMPLE 8

A solution 0.4 molar in each of (5-methyl-1H-imidazol-4-yl)thiol of formula XXI, N-(3-bromopropyl)-phthalimide and potassium hydroxide in methanol as solvent is refluxed overnight.

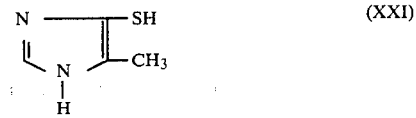

After cooling the reaction mixture, the methanol is removed by evaporation, leaving a product which solidified upon slurrying with water. The solid is filtered, dried and recrystallized from a methylene chloride/Skelly B solvent to afford the compound of formula XXII

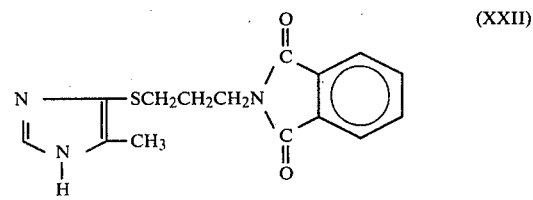

A solution 0.11 molar in each of the intermediate of formula XXII and hydrazine hydrate in 95 percent ethanol is then refluxed for 1 hour at which time additional hydrazine hydrate in an amount half that originally added is added and the solution is refluxed for another hour. After allowing the reaction mixture to stand at room temperature overnight, the mixture is filtered, and the filtrate is stripped to dryness and then mixed with a volume of ethanol equal to that in the original ethanol solution and filtered again. The resulting material, 3-[(5-(1-methylethyl)-1H-imidazol-4-yl)-thio]propan-1-amine, is converted to its dihydrochloride of formula XXIII by reaction with dilute hydrochloric acid.

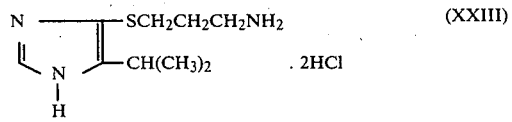

EXAMPLE 9

Repeating the procedure of Example 2 using the product of Example 8 instead of the dihydrochloride therein and the product of Example 7 instead of the product of Example 1, N-cyano-N'-[3-(4-methoxyphenyl)-2-propen-1-yl]-N''-[3-((5-(1-methylethyl)-1H-imidazol-4-yl)thio)prop-1-yl] guanidine hydrochloride of formula XXIV is formed as the final product.

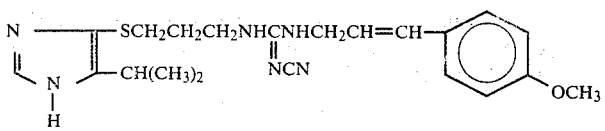 (XXIV)

EXAMPLE 10

Repeating the procedure of Example 2 using 2-[((5-methylthiazol-4-yl)methyl)thio]elthanamine dihydrochloride of formula XXV

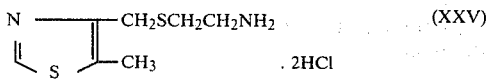 (XXV)

instead of the dihydrochloride therein, N-cyano-N'-[2-(((5-methylthiazol-4-yl)methyl)thio)ethyl]-N''-(3-phenyl-2-propen-1-yl)-guanidine hydrochloride of formula XXVI is formed as the final product.

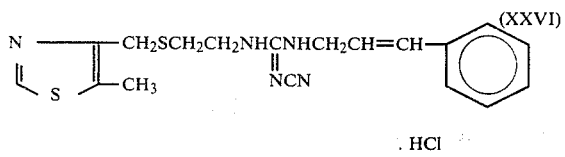 (XXVI)

EXAMPLE 11

Repeating the procedure of Example 2 using 3-[((thiazol-4-yl)-methyl)thio]propan-1-amine dihydrochloride instead of the dihydrochloride therein, N-cyano-N'-(3-phenyl-2-propen-1-yl)-N''-[3-(((thiazol-4-yl)methyl)thio)prop-1-yl]-guanidine hydrochloride is formed as the final product.

EXAMPLE 12

To a solution which is 5 molar in 2,3-dihydro-1,4-benzodioxin-6-carboxaldehyde of formula XXVII

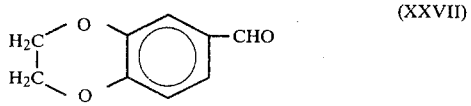 (XXVII)

and 0.58 molar in potassium hydroxide in ethanol as the solvent is added acetaldehyde in an amount sufficient to make the solution nominally 4 molar in acetaldehyde, over a period of 20 minutes and while stirring at 10° C. After the mixture is stirred at 10° C. for an additional 10 minutes, it is acidified by the addition of glacial acetic acid. Water is then added and the insoluble oil formed is extracted with ether. The ether solution is washed with water, dried and distilled to yield 3-(2,3-dihydro-1,4-benzodioxin-6-yl)-2-propenal of formula XXVIII

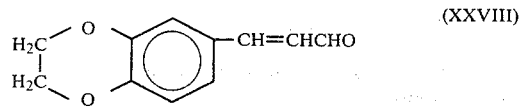 (XXVIII)

A solution 0.33 molar in aluminum isopropoxide in isopropyl alcohol is made 0.11 molar in the propenal of formula XXVIII and the mixture is refluxed for 10 hours. During this time acetone is allowed to distill off slowly as it forms. The mixture is then vacuum-distilled to remove most of the isopropyl alcohol, and the residual oil is treated with cold, dilute sulfuric acid. The mixture is extracted with ether, and the ether solution is washed with water, dried and fractionated by distillation. The fraction comprising 3-(2,3-dihydro-1,4-benzodioxin-6-yl)-2-propen-1-ol of formula XXIX is collected.

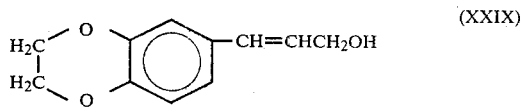 (XXIX)

A 2.99 molar solution of the 2-propen-1-ol of formula XXIX in chloroform is added to an equal volume of a cooled 17.5 molar solution of thionyl chloride in chloroform. The mixture is allowed to warm to room temperature and then is distilled, to yield 3-chloro-1-(2,3-dihydro-1,4-benzodioxin-6-yl)-1-propene of formula XXX.

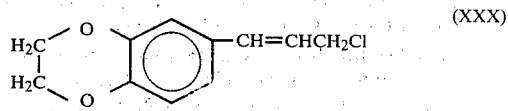 (XXX)

A solution 0.4 molar in each of the 3-chloro-1-propene of formula XXX, potassium phthalimide and potassium hydroxide in ethanol as solvent is refluxed overnight. After cooling the reaction mixture, the ethanol is removed by evaporation, leaving a product which solidifies upon slurrying with water. The solid is filtered, dried and recrystallized from a methylene chloride/Skelly B solvent to afford the compound of formula XXXI

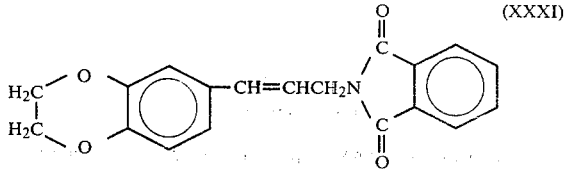 (XXXI)

A solution 0.11 molar in each of the intermediate of formula XXXI and hydrazine hydrate in 95 percent ethanol is then refluxed for 1 hour at which time additional hydrazine hydrate in an amount half that originally added is added and the solution is refluxed for another hour. After allowing the reaction mixture to stand at room temperature overnight, the mixture is filtered, and the filtrate is stripped to dryness and then mixed with a volume of ethanol equal to that in the original ethanol solution and filtered again. Removal of the solvent from the filtrate affords 3-(2,3-dihydro-1,4-benzodioxin-6-yl)-2-propen-1-amine, which is then converted to its hydrochloride of formula XXXII by acidification with dilute hydrochloric acid.

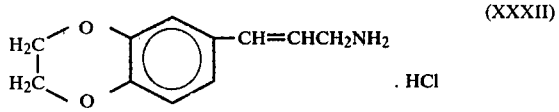

(XXXII)

EXAMPLE 13

Repeating the procedure of Example 1 using the product of Example 12 instead of the hydrochloride therein, N-cyano-N'-[3-(2,3-dihydro-1,4-benzodioxin-6-yl)-2-propen-1-yl]carbamimidothioic acid, methyl ester of formula XXXIII is formed as the product

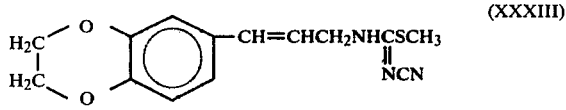

(XXXIII)

EXAMPLE 14

Repeating the procedure of Example 2 using 2-[(2-(5-ethylthiazol-4-yl)ethyl)thio]ethanamine dihydrochloride instead of the dihydrochloride therein and the product of Example 13 instead of the product of Example 1, N-cyano-N'-[3-(2,3-dihydro-1,4-benzodioxin-6-yl)-2-propen-1-yl]-N''-[2-((2-(5-ethylthiazol-4-yl)ethyl)thio)ethyl]-guanidine hydrochloride of formula XXXIV is formed as the final product.

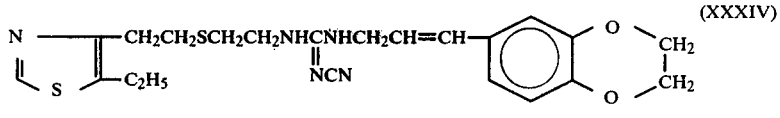

(XXXIV)

EXAMPLE 15

Repeating the procedure of Example 12 using 4-methylaminobenzaldehyde instead of the starting material of formula XXVII therein and replacing the intermediates of formulas XXVIII–XXXI with corresponding intermediates formed from 4-methylaminobenzaldehyde, 3-(4-methylaminophenyl)-2-propen-1-amine dihydrochloride is formed.

EXAMPLE 16

Repeating the procedure of Example 1 using 3-(4-methylaminophenyl)-2-propen-1-amine dihydrochloride instead of the hydrochloride therein and potassium hydroxide in twice the molar amount of the dihydrochloride, N-cyano-N'-[3-(4-methylaminophenyl)-2-propen-1-yl]-carbamimidothioic acid, methyl ester is formed as the product.

EXAMPLE 17

Repeating the procedure of Example 2 using 2-[((5-methyloxazol-4-yl)methyl)thio]ethanamine dihydrochloride of formula XXXV

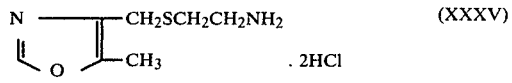

(XXXV)

instead of the dihydrochloride therein and the product of Example 16 instead of the product of Example 1, N-cyano-N'-[3-(4-methylaminophenyl)-2-propen-1-yl]-N''-[2-(((5-methyloxazol-4-yl)methyl)thio)ethyl]-guanidine dihydrochloride of formula XXXVI is formed as the final product.

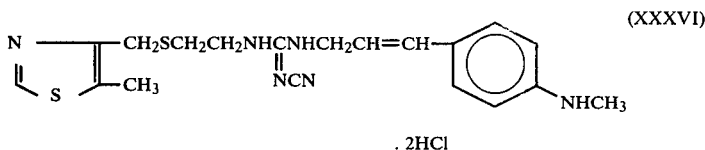

(XXXVI)

EXAMPLE 18

Repeating the procedure of Example 2 using 2-[(oxazol-4-yl)methylthio]-ethanamine dihydrochloride instead of the dihydrochloride therein, N-cyano-N'-[2-((oxazol-4-yl)methylthio)ethyl]-N''-(3-phenyl-2-propen-1-yl)-guanidine hydrochloride is formed as the final product.

EXAMPLE 19

Repeating the procedure of Example 2 using 3-[((oxazol-4-yl)methyl)thio]propan-1-amine dihydrochloride instead of the dihydrochloride therein and the product of Example 3 instead of the product of Example 1, N-cyano-N'-[3-(4-hydroxyphenyl)-2-propen-1-yl]-N''-[3-(((oxazol-4-yl)-methyl)thio)prop-lyl]guanidine hydrochloride is formed as the final product.

EXAMPLE 20

Repeating the procedure of Example 12 using 4-acetylaminobenzaldehyde instead of the starting material of formula XXVII therein and replacing the intermediates of formulas XXVIII–XXXI with corresponding intermediates formed from 4-acetylaminobenzaldehyde, 3-(4-acetylaminophenyl-2-propen-1-amine hydrochloride is formed.

EXAMPLE 21

Repeating the procedure of Example 1 using 3-(4-acetylaminophenyl)-2-propen-1-amine hydrochloride instead of the hydrochloride therein, N-[3-(4-acetylaminophenyl)-2-propen-1-yl]-N'-cyanocarbamimidothioic acid, methyl ester is formed as the product.

EXAMPLE 22

Repeating the procedure of Example 2 using 2-[((2-(diaminomethylene)amino-1H-imidazol-4-yl)methyl)-thio]-ethanamine dihydrochloride of formula XXXVII

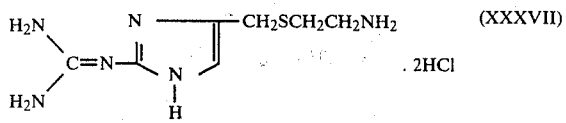

instead of the dihydrochloride therein and the product of Example 21 instead of the product of Example 1, N-[3-(4-acetylaminophenyl)-2-propen-1-yl]-N'-cyano-N''[2-(((2-(diaminomethylene)amino-1H-imidazol-4-yl)methyl)thio)-ethyl]-guanidine hydrochloride of formula XXXVIII is formed as the final product.

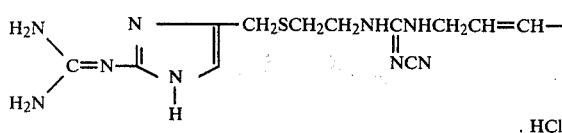 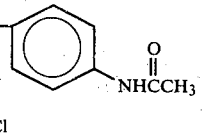

EXAMPLE 23

Repeating the procedure of Example 2 using 2-[((2-(amino(methylamino)methylene)amino-1H-imidazol-4-yl)-methyl)thio]ethanamine dihydrochloride instead of the dihydrochloride therein, N-[2-(((2-(amino(methylamino)methylene)amino-1H-imidazol-4-yl)-methyl)thio)ethyl]-N-cyano-N''-[3-phenyl-2-propen-1-yl]-guanidine hydrochloride is formed as the final product.

EXAMPLE 24

Repeating the procedure of Example 12 using 4-chloro-3-methoxybenzaldehyde of formula XXXIX

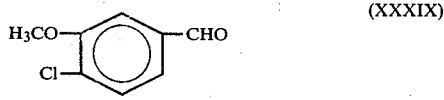

instead of the starting material of formula XXVII therein and replacing the intermediates of formulas XXVIII—XXXI with corresponding intermediates formed from 4-chloro-3-methoxybenzaldehyde, 3-(4-chloro-3-methoxyphenyl)-2-propen-1-amine hydrochloride is formed.

EXAMPLE 25

Repeating the procedure of Example 1 using the product of Example 24 instead of the hydrochloride therein, N-[3-(4-chloro-3-methoxyphenyl)-2-propen-1-yl]-N'cyanocarbamimidothioic acid, methyl ester is formed as the product.

EXAMPLE 26

Repeating the procedure of Example 2 using 2-[(2-(2-(amino(methylamino)methylene)amino-1H-imidazol-4-yl)ethyl)thio]ethanamine dihydrochloride instead of the dihydrochloride therein and the product of Example 25 instead of the product of Example 1, N-[2-((2-(2-(amino(methylamino)methylene)amino-1H-imidazol-4-yl)ethyl)thio)-ethyl]-N'-[3-(4-chloro-3-methoxyphenyl)-2-propen-1-yl]-N''-cyano-guanidine dihydrochloride is formed as the final product.

EXAMPLE 27

Repeating the procedure of Example 12 using 4-(phenylmethyl)aminobenzaldehyde instead of the starting material of formula XXVII therein and replacing the intermediates of formulas XXVIII–XXXI with corresponding intermediates formed from 4-(phenylmethyl)aminobenzaldehyde, 3-[4-(phenylmethyl)aminophenyl]-2-propen-1-amine hydrochloride is formed.

EXAMPLE 28

Repeating the procedure of Example 1 using the product of Example 27 instead of the hydrochloride therein, N-cyano-N'-[3-(4-phenylmethyl)aminophenyl)-2-propen-1-yl]-carbamimidothioic acid, methyl ester is formed as the product.

EXAMPLE 29

Repeating the procedure of Example 2 using 3-[((2-((amino-(ethylamino)methylene)amino)thiazol-4-yl)-methyl)thio]-2-propen-1-amine dihydrochloride instead of the dihydrochloride therein and the product of Example 28 instead of the product of Example 1. N-[3-(((2-((amino(ethylamino)-methylene)amino)thiazol-4-yl)methyl)thio)-prop-1-yl]-N'-cyano-N''-[3-(4-(phenylmethyl)aminophenyl)-2-propen-1-yl]quanidine hydrochloride is formed as the final product.

EXAMPLE 30

Repeating the procedure of Example 12 using 4-phenylmethoxybenzaldehyde instead of the starting material of formula XXVII therein and replacing the intermediates of formulas XXVIII–XXXI with corresponding intermediates formed from 4-phenylmethoxybenzaldehyde, 3-(4-phenylmethoxyphenyl)-2-propen-1-amine hydrochloride is formed.

EXAMPLE 31

Repeating the procedure of Example 1 using the product of Example 30 instead of the hydrochloride therein, N-cyano-N'-[3-(4-phenylmethoxyphenyl)-2-propen-1-yl]-carbamimidothioic acid, methyl ester is formed as the product.

EXAMPLE 32

Repeating the procedure of Example 2 using 2-[((2-((amino(prop-1-ylamino)methylene)amino)thiazol-4-yl)methyl)thio]ethanamine dihydrochloride instead of the dihydrochloride therein and the product of Example 31 instead of the product of Example 1, N-[2-(((2-((amino(prop-1-ylamino)methylene)amino)thiazol-4-yl)methyl)thio)ethyl]-N'-cyano-N''-[3-(4-phenylmethoxyphenyl)-2-propen-1-yl]-guanidine hydrochloride is formed as the final product.

EXAMPLE 33

Repeating the procedure of Example 2 using 2-[((2-((diaminomethylene)amino)oxazol-4-yl)methyl)thio]-ethanamine dihydrochloride instead of the dihydrochloride therein and the product of Example 5 instead of the product of Example 1, N-[3-(4-chlorophenyl)-2-propen-1-yl]-N'-cyano-N''-[2-(((2-((diaminomethylene)amino)oxazol-4-yl)methyl)thio)-ethyl]-guanidine hydrochloride is formed as the final product.

EXAMPLE 34

Repeating the procedure of Example 2 using 2[((2-((diaminomethylene)amino)oxazol-4-yl)methyl)thio]-ethanamine dihydrochloride instead of the dihydrochloride therein, N-cyano-N'-[2-(((2-((diaminomethylene)amino)oxazol-4-yl)methyl)thio)ethyl]-N''-(3-phenyl-2-propen-1-yl)-guanidine hydrochloride is formed as the final product.

EXAMPLE 35

Repeating the procedure of Example 2 using 2-[((5-((dimethylamino)methyl)-furan-2-yl)methyl)thio]ethanamine dihydrochloride of formula XL

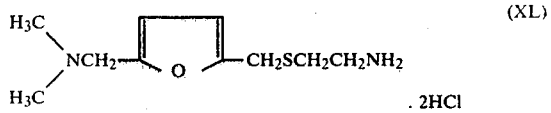

. 2HCl (XL)

instead of the dihydrochloride therein, N-cyano-N'-[2-(((5-((dimethylamino)methyl)furan-2-yl)methyl)thio)ethyl]-N''-(3-phenyl-2-propen-1-yl) guanidine hydrochloride of formula XLI is formed as the final product.

EXAMPLE 36

Repeating the procedure of Example 2 using 2-[((5-(((phenylmethyl)amino)methyl)-furan-2-yl)methyl)thio]-ethanamine dihydrochloride instead of the dihydrochloride therein and the product of Example 3 instead of the product of Example 1, N-cyano-N'-[3-(4-hydroxyphenyl)-2-propen-1-yl]-N''-[2-(((5-(((phenylmethyl)amino)methyl)-furan-2-yl)methyl)-thio)ethyl]-guanidine hydrochloride is formed as the final product.

EXAMPLE 37

Repeating the procedure of Example 8 using (5-(4-morpholinylmethyl)-furan-2-yl)thiol of formula XLII

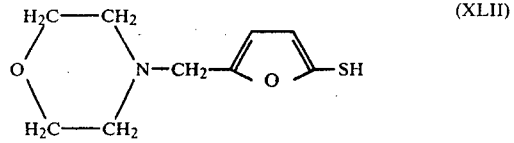

(XLII)

instead of the starting material of formula XXI therein and replacing the intermediate of formula XXII with a corresponding intermediate formed from (5-(4-morpholinylmethyl)-furan-2-yl)thiol, 3-[(5-(4-morpholinylmethyl)-furan-2-yl)-thio] propan-1-amine dihydrochloride of formula XLIII is formed.

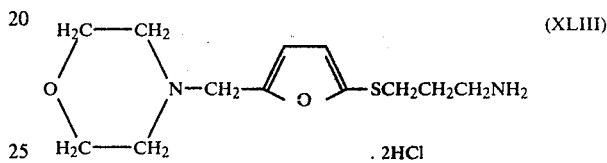

(XLIII)

EXAMPLE 38

Repeating the procedure of Example 10 using the product of Example 37 instead of the dihydrochloride therein and the product of Example 5 instead of the product of Example 1, N-[3-(4-chlorophenyl)-2-propen-1-yl]-N'-cyano-N''-[3-((5-(4-morpholinylmethyl)-furan-2-yl)-thio)-1-prop-1-yl]-guanidine hydrochloride of formula XLIV is formed as the final product.

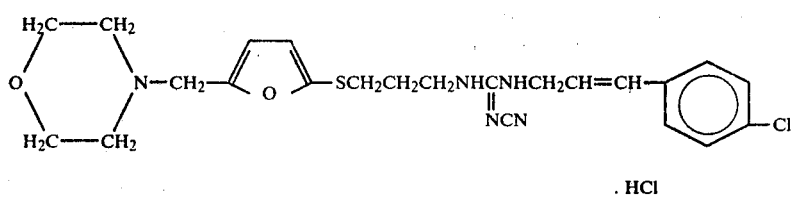

(XLIV)

. HCl

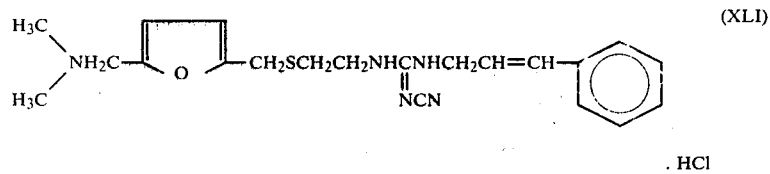

(XLI)

. HCl

From the above description it is apparent that the objects of the present invention have been achieved. While only certain embodiments have been set forth, it will be apparent to those skilled in the art that many modifications, both of materials and methods, may be practiced without departing from the purpose and intent of this disclosure.

Having described the invention, what is claimed is:
1. A compound of the formula $$A(CH_2)_d S(CH_2)_e NHCNHCH_2CH=CH-\underset{R_2}{\overset{R_1}{\bigcirc}}$$
$$\overset{\|}{NCN}$$

or a pharmacologically acceptable salt thereof, wherein A is of the formula:

1. $\underset{X}{\overset{N}{\underset{\|}{\bigcirc}}}-R_3$

2. $\underset{H_2N}{\overset{HR_4N}{\diagdown}}C=N-\underset{X}{\overset{N}{\bigcirc}}$ or 3. $R_7R_6NR_5-\underset{O}{\bigcirc}$ wherein $R_1$ and $R_2$ can be the same or different and each represents hydrogen, halogen, hydroxy, trifluoromethyl, alkoxy containing 1 to 7 carbon atoms and either unsubstituted or substituted by aryl or cycloalkyl, or amino either unsubstituted or substituted with at least one acyl or alkyl, each containing 1 to 7 carbon atoms, the alkyl being unsubstituted or substituted by aryl or cycloalkyl; or $R_1$ and $R_2$ are interconnected forming a group having terminal oxygen atoms which are separated by methylene or ethylene and which are attached to adjacent carbon atoms on the phenyl ring;

X represents —O—, —S—, or —N—;

$R_3$ represents hydrogen, halogen or alkyl containing 1 to 7 carbon atoms:

$R_4$ represents hydrogen or alkyl containing 1 to 7 carbon atoms when X is —S— or $$-\underset{H}{\overset{-N-}{|}}$$

and represents hydrogen when S is O;

$R_5$ is alkylene of 1 to 6 carbon atoms;

$R_6$ and $R_7$ can be the same or different and each represents hydrogen, cycloalkyl or alkyl, each containing 1 to 7 carbon atoms, the alkyl ether unsubstituted or substituted by aryl; or $R_6$ and $R_7$ are interconnected forming with the nitrogen atom in formula 3 a 5- or 6- membered ring which can include oxygen; and d is 0, 1 or 2 and e is 2 or 3 when A is of formula 1 or 3; d is 1 or 2 and e is 2 or 3 when A is of formula 2 and X is —S— or $$-\underset{H}{\overset{-N-}{|}};$$

d is 1 and e is 2 when A is of formula 2 and X is —O—; and the sum of d and e is 3 or 4.

2. The compound of claim 1 wherein d is 1.
3. The compound of claim 1 wherein e is 2.
4. The compound of claim 1 wherein A is imidazol-4-yl.
5. The compound of claim 1 wherein $R_1$ is hydrogen, hydroxy, halogen, methoxy, phenylmethoxy or amino substituted with acetyl, methyl, or phenylmethyl.
6. The compound of claim 1 wherein $R_2$ is hydrogen, hydroxy, halogen, methoxy, phenylmethoxy or amino substituted with acetyl, methyl or phenylmethyl.
7. The compound of claim 1 wherein $R_1$ and $R_2$ are interconnected forming a group having terminal oxygen atoms separated by methylene.
8. The compound of claim 1 wherein A is of formula 1 and $R_3$ is hydrogen or methyl.
9. The compound of claim 1 wherein A is of formula 2 and $R_4$ is hydrogen or methyl.
10. The compound of claim 1 wherein A is of formula 3 and $R_5$ is methylene.
11. The compound of claim 1 wherein A is of formula 3 and $R_6$ is hydrogen or methyl.
12. The compound of claim 1 wherein A is of formula 3 and $R_7$ is hydrogen or methyl.
13. The compound of claim 1 wherein A is of formula 3, $R_6$ is methyl and $R_7$ is hydrogen.
14. The compound of claim 1 wherein A is of formula 3 and $R_6$ and $R_7$ are each methyl.
15. The compound of claim 1 wherein A is of formula 3 and $R_6$ and $R_7$ are interconnected forming tetramethylene or pentamethylene.
16. The compound of claim 1 being N-cyano-N'-[2-(((5-methyl-1H-imidazol-4-yl)methyl)thio)ethyl]-N''-(3-phenyl-2-propen-1-yl)guanidine hydrochloride.

* * * * *